United States Patent [19]

Casado et al.

[11] Patent Number: 5,432,290
[45] Date of Patent: Jul. 11, 1995

[54] PROCESS FOR THE PREPARATION OF 2,2-DIFLUORO-1,3-BENZODIOXOLE

[75] Inventors: Michel Casado, St-Symphorien d'Ozon; Michel Crochemore, Chaponost; Bernard Langlois, Lyons, all of France

[73] Assignee: Rhone-Poulenc Chimie, Courbevoie, France

[21] Appl. No.: 51,281

[22] Filed: Jan. 21, 1992

Related U.S. Application Data

[63] Continuation of Ser. No. 592,466, Oct. 3, 1990, abandoned.

[30] Foreign Application Priority Data

Oct. 9, 1989 [FR] France .................. 89 13369

[51] Int. Cl.⁶ .......................... C07D 317/46
[52] U.S. Cl. .................................. 549/434
[58] Field of Search ........................ 549/434

[56] References Cited

U.S. PATENT DOCUMENTS

| | | | |
|---|---|---|---|
| 4,110,345 | 8/1978 | Berkelhammer et al. | 549/434 |
| 4,438,275 | 3/1984 | Lantzsch et al. | 549/434 |
| 4,600,787 | 7/1986 | Marhold et al. | 549/434 |
| 4,692,166 | 9/1987 | Junino et al. | 549/434 |

FOREIGN PATENT DOCUMENTS

| | | |
|---|---|---|
| 0006987 | 1/1980 | European Pat. Off. . |
| 0333661 | 9/1989 | European Pat. Off. ........... 549/434 |
| 3642256A1 | 6/1987 | Germany . |

OTHER PUBLICATIONS

Chem. Berichte vol. 96, 1382 (1963).

*Primary Examiner*—C. Warren Ivy
*Assistant Examiner*—A. A. Owens
*Attorney, Agent, or Firm*—Finnegan, Henderson, Farabow, Garrett & Dunner

[57] ABSTRACT

A process for the preparation of 2,2-difluoro-1,3-benzodioxole from 2,2-dichloro1,3-benzodioxole. 2,2-Difluoro-1,3-benzodioxole is prepared by reaction of 2,2-dichloro-1,3-benzodioxole with potassium fluoride in the presence of an effective quantity of a catalyst selected from potassium hydrogen fluoride, sodium hydrogen fluoride, cesium hydrogen fluoride, rubidium hydrogen fluoride, and quaternary ammonium hydrogen fluoride. 2,2-Difluoro-1,3-benzoxodiole is an intermediate compound which is used particularly for the preparation of products for agricultural chemistry and for the synthesis of pharmaceutical products.

17 Claims, No Drawings

PROCESS FOR THE PREPARATION OF 2,2-DIFLUORO-1,3-BENZODIOXOLE

This application is a continuation of application Ser. No. 07/592,466, filed Oct. 3, 1990 now abandoned.

The present invention relates to a process for the preparation of 2,2-difluoro-1,3-benzodioxole from 2,2-dichloro-1,2-benzodioxole.

Patent EP-A-0,006,987 describes the chlorine-fluorine exchange in the 2,2-dichloro-1,3-benzodioxole molecule by means of liquid hydrogen fluoride, generally at temperatures of −10° C. to 0° C. 2,2-Difluoro-1,3-benzoxodiole is an intermediate compound which is used particularly for the preparation of products for agricultural chemistry and for the synthesis of pharmaceutical products.

The yields obtained are good but, nevertheless, research is still carried on to improve them. Moreover, the technique of synthesis of HF requires specific hardware which is not available at all industrial sites.

It is an object of the present invention to improve further the yield when converting 2,2-dichloro-1,3-benzodioxole into 2,2-difluoro-1,3-benzodioxole.

More precisely, the present invention comprises a process for the preparation of 2,2-difluoro-1,3-benzodioxole by reaction of 2,2-dichloro-1,3-benzodioxole with potassium fluoride in the presence of an effective amount of a catalyst selected from potassium hydrogen fluoride ($KHF_2$); sodium hydrogen fluoride ($NaHF_2$); cesium hydrogen fluoride ($CsHF_2$); rubidium hydrogen fluoride ($RbHF_2$); and quaternary ammonium hydrogen fluoride ($NR_4HF_2$) where R may be the same or different and is selected from hydrogen, alkyl, heteroalkyl, aryl and heteroaryl. Preferably R is methyl or benzyl and most preferably $NR_4$ is benzyltrimethyl ammonium. The catalyst employed is preferably potassium hydrogen fluoride, $KHF_2$.

The preferred $KHF_2$ catalyst can be generated in the reaction mixture from potassium fluoride in the presence of small quantities of water. In fact, this water, which can particularly come from the potassium fluoride when the latter is not perfectly anhydrous, reacts with 2,2-dichloro-1,3-benzodioxole to form pyrocatechol carbonate and generates hydrogen chloride to give, with potassium fluoride, potassium hydrogen fluoride and potassium chloride. This catalyst can also be generated in the reaction mixture from potassium fluoride, by introducing an anhydrous strong acid such as hydrogen chloride or hydrogen bromide.

It is nevertheless more convenient to introduce potassium hydrogen fluoride as catalyst, because this makes it possible to control the quantity used. An unnecessary consumption of 2,2-dichloro-1,3-benzodioxole is also avoided in this way.

However, one of the advantages of the process of the invention is that it can be carried out even in the presence of traces of water.

The quantity of potassium fluoride represents at least substantially the stoichiometric amount needed to form 2,2-difluoro-1,3-benzodioxole. The molar ratio KF/2,2-dichloro-1,3-benzodioxole is preferably from 2:1 to 4:1, more preferably from 2:1 to 3.4:1 and most preferably 2:1 to 2.5:1.

The quantity of catalyst and more particularly of the preferred $KHF_2$ is preferably between 0.5 and 50% by weight relative to the weight of 2,2-dichloro-1,3-benzodioxole introduced. The catalyst more preferably represents from 5% to 20% by weight relative to 2,2-dichloro-1,3-benzodioxole.

The reaction is usually carried out in solution. The solvent employed can preferably be a polar aprotic solvent. Nonlimiting examples of very preferred suitable solvents which can be mentioned are tetramethylene sulfone (or sulfolane) and acetonitrile.

The initial concentration of 2,2-dichloro-1,3-benzodioxole in the solvent may vary widely and is not critical. Generally, if the weight of 2,2-dichloro-1,3-benzodioxole is expressed in relation to the total weight of solvent and 2,2-dichloro-1,3-benzodioxole, it is from 10% to 50% and preferably from 15% to 40%.

The temperature at which the chlorine-fluorine exchange reaction is carried out may also vary within wide limits, for example, preferably between 80° and 250° C. To have sufficiently fast kinetics while avoiding as much as possible any degradation of the reactants, the operation is more preferably carried out between 100° C. and 200° C.

2,2-Dichloro-1,3-benzodioxole is a known product. It can be obtained particularly by photochlorination of 1,2-methylenedioxybenzene with the aid of gaseous chlorine in a chlorinated hydrocarbon and in the presence of an organic phosphate such as tributyl phosphate. Reference can also be made in the case of this preparation to the paper in the Journal of Chemical Society vol. 93, page 566 (1908). 2,2-Dichloro-1,3-benzodioxole can also be obtained from pyrocatechol carbonate as described in Chem. Berichte vol. 96, 1382 (1963).

2,2-Difluoro-1,3-benzodioxole is an intermediate compound which is used particularly for the preparation of products for agricultural chemistry and for the synthesis of pharmaceutical products.

The examples which follow illustrate, but do not limit, the invention.

EXAMPLE 1

The following are charged into a glass three-necked round bottom flask fitted with a central stirrer, a vertical condenser and means of heating:

210 g (3.61 mol) of anhydrous KF (dried in vacuum at 150° C.)
23 g of $KHF_2$ (dried over $P_2O_5$)
500 g of tetramethylene sulfone (distilled over molecular sieves)
226 g (1.18 mol) of 2,2-dichloro-1,3-benzodioxole.

These are heated to 140° C. while being stirred and the progress of the reaction is followed by sampling at regular intervals and making determinations using gas chromatography (GC).

After 8 hours the reaction is complete: the degree of conversion of 2,2-dichloro-1,3-benzodioxole is 100%.

The reaction mixture is cooled; 2000 g of water are added to dissolve the salts and the tetramethylene sulfone: an organic phase consisting essentially of 2,2-difluoro-1,3-benzodioxole separates out and is purified by distillation.

155 g (0.98 mol) of isolated pure 2,2-difluoro-1,3-benzodioxole are obtained, which represents an 83% yield (RY %) based on the 2,2-dichloro-1,3-benzodioxole introduced.

EXAMPLE 2

The following are charged into a 30 cm³ glass tube fitted with a Teflon stopper, a magnetic stirrer and a heating system:

2.95 g (0.015 mol) of 2,2-dichloro-1,3-benzodioxole
6.5 g of tetramethylene sulfone
2.95 g (0.050 mol) of anhydrous KF
0.3 g of KHF$_2$.

These are heated to 140° C. for 7 hours with stirring. The products obtained are determined using GC.

| | |
|---|---|
| Degree of conversion (DC %) of 2,2-dichloro-1,3-benzodioxole: | 100% |
| RY % of 2-chloro-2-fluoro-1,3-benzodioxole | 5% |
| RY % of 2,2-difluoro-1,3-benzodioxole: | 95% |

Comparative Test A

Example 2 is repeated, but omitting the KHF$_2$ catalyst. The following results are obtained:

| | |
|---|---|
| DC % of 2,2-dichloro-1,3-benzodioxole: | 93% |
| RY % of 2-chloro-2-fluoro-1,3-benzodioxole: | 91% |
| RY % of 2,2-difluoro-1,3-benzodioxole: | 2% |

EXAMPLE 3

Example 2 is repeated under the same conditions and with the same reactants, but using 0.05 g of water replacing the KHF$_2$.

After 7 hours' heating at 140° C., the following results are obtained:

| | |
|---|---|
| DC % of 2,2-dichloro-1,3-benzodioxole: | 100% |
| RY % of 2-chloro-2-fluoro-1,3-benzodioxole: | 0% |
| RY % of 2,2-difluoro-1,3-benzodioxole: | 66% |

In addition, 20% of pyrocatechol carbonate is found, relative to the starting 2,2-dichloro-1,3-benzodioxole.

EXAMPLE 4

Example 2 is repeated under the same conditions and with the same reactants, but using 0.1 g of gaseous HCl replacing the KHF$_2$.

After 7 hours' heating at 140° C., the following results are obtained:

| | |
|---|---|
| DC % of 2,2-dichloro-1,3-benzodioxole: | 100% |
| RY % of 2-chloro-2-fluoro-1,3-benzodioxole: | 1% |
| RY % of 2,2-difluoro-1,3-benzodioxole: | 83% |

EXAMPLE 5

Example 2 is repeated under the same conditions and with the same reactants, but using 0.3 g of benzyltrimethylammonium hydrogen fluoride replacing the KHF$_2$.

After 7 hours' heating at 140° C. the following results are obtained:

| | |
|---|---|
| DC % of 2,2-dichloro-1,3-benzodioxole: | 100% |
| RY % of 2-chloro-2-fluoro-1,3-benzodioxole: | 1% |
| RY % of 2,2-difluoro-1,3-benzodioxole: | 81% |

What is claimed is:

1. A process for the preparation of 2,2-difluoro-1,3-benzodioxole comprising the step of:
   reacting 2,2-dichloro-1,3-benzodioxole with potassium fluoride in the presence of a catalyst selected from the group consisting of potassium hydrogen fluoride, sodium hydrogen fluoride, cesium hydrogen fluoride, rubidium hydrogen fluoride and quaternary ammonium hydrogen fluoride, for a time sufficient to obtain said 2,2-difluoro-1,3-benzodioxole, wherein the catalyst is present in an amount of between 0.5% and 50% by weight relative to the 2,2-dichloro-1,3-benzodioxole.

2. The process as claimed in claim 1, wherein the catalyst employed is potassium hydrogen fluoride.

3. The process as claimed in claim 1, wherein the molar ratio KF/2,2-dichloro-1,3-benzodioxole is from 2:1 to 4:1.

4. The process as claimed in claim 3, wherein the molar ratio of KF/2,2-dichloro-1,3-benzodioxole is from 2:1 to 2.5:1.

5. The process as claimed in claim 1, wherein the catalyst is potassium;hydrogen fluoride.

6. The process as claimed in claim 5, wherein the quantity of catalyst is between 5% and 20% by weight.

7. The process as claimed in claim 1, wherein the quantity of catalyst is between 5% and 20% by weight.

8. The process as claimed in claim 1, wherein the reaction is carried out in solution in a polar aprotic solvent.

9. The process as claimed in claim 8, wherein the solvent employed is selected from the group consisting of tetramethylene sulfone and acetonitrile.

10. The process as claimed in claim 8, wherein the initial concentration of 2,2-dichloro-2,3-benzodioxole in the solvent, expressed as the weight of 2,2-dichloro-1,3-benzodioxole in relation to the total weight of solvent and 2,2-dichloro-1,3-benzodioxole, is from 10% to 50% by weight.

11. The process as claimed in claim 10, wherein the initial concentration of 2,2-dichloro-2,3-benzodioxole in the solvent is from 15% to 40% by weight.

12. The process as claimed in claim 1, wherein the temperature at which the chlorine-fluorine exchange reaction is carried out is between 80° and 250° C.

13. The process as claimed in claim 12 wherein the temperature is between 100° C. and 200° C.

14. The process as claimed in claim 9, wherein the catalyst is potassium hydrogen fluoride.

15. The process as claimed in claim 10, wherein the catalyst is potassium hydrogen fluoride.

16. The process as claimed in claim 12, wherein the catalyst is potassium hydrogen fluoride.

17. The process as claimed in claim 2, wherein the potassium hydrogen fluoride catalyst is generated in situ using water or a strong acid.

* * * * *